United States Patent [19]
Ishida

[11] Patent Number: 5,590,009
[45] Date of Patent: Dec. 31, 1996

[54] MAGNETIC DISK UNIT

[75] Inventor: Takehisa Ishida, Tokyo, Japan

[73] Assignee: Sony Corporation, Tokyo, Japan

[21] Appl. No.: 445,123

[22] Filed: May 19, 1995

Related U.S. Application Data

[63] Continuation of Ser. No. 126,456, Sep. 24, 1993, abandoned.

[30] Foreign Application Priority Data

Sep. 30, 1992 [JP] Japan .................................. 4-285209

[51] Int. Cl.$^6$ ........................................................ G11B 5/82
[52] U.S. Cl. ................................................................ 360/135
[58] Field of Search ................................... 360/135, 131, 360/128, 78.05, 77.08, 77.11, 77.03, 77.05, 64; 369/289, 290, 283

[56] References Cited

U.S. PATENT DOCUMENTS

| | | | |
|---|---|---|---|
| 4,562,105 | 12/1985 | Machida et al. | 360/135 |
| 4,656,538 | 4/1987 | Mattson | 360/77.08 |
| 4,672,470 | 6/1987 | Morimoto et al. | 358/323 |
| 4,737,869 | 4/1988 | Sugaya et al. | 360/135 |
| 4,911,967 | 3/1990 | Iazzari | 360/135 |
| 5,051,851 | 9/1991 | Sakurai . | |
| 5,065,382 | 11/1991 | Seko et al. | 360/77.08 |
| 5,138,511 | 8/1992 | Hoshimi et al. . | |
| 5,235,478 | 8/1993 | Hoshimi et al. | 360/135 |
| 5,296,995 | 3/1994 | Yonezawa et al. | 360/77.03 |
| 5,317,468 | 5/1994 | Wakabayashi et al. | 360/135 |

FOREIGN PATENT DOCUMENTS 9107255  9/1991  Germany .

OTHER PUBLICATIONS

Journal of Applied Physics, Lambert, S. E. et al. 'Beyond Discrete Tracks: Other Aspects of Patterned Media' pp. 4724–4726, Apr. 15, 1991, NY, USA.

VLSI and Computer Peripherals, Sanders, I. L. et al. 'Discrete Tracks—Possibilities for High–Density Magnetic Disks?' pp. 1–12 to 1–15, May 8, 1989, Hamburg.

Patent Abstracts of Japan vol. 014 No. 098 (P–1011), 22 Feb. 1990 & JP–A–01 302532 (Toa Nenryo Kogyo KK) 6 Dec. 1989, * abstract *.

Patent Abstracts of Japan vol. 14 No. 183 (P–1035) [4126], 12 Apr. 1990 & JP–A–02 031323 (Asahi Glass Co. Ltd.) 1 Feb. 1990 * abstract *.

IEEE Transactions on Magnetics, vol. 24, No. 6, Nov. 1988, pp. 2958–2960, "A Novel Way of Formatting To Accommodate Variations in Heads and Media", Jackson et al.

*Primary Examiner*—Stuart S. Levy
*Assistant Examiner*—Allen Cao
*Attorney, Agent, or Firm*—Pasquale Musacchio, Esq.; Jerry A. Miller; Peter C. Toto, Esq.

[57] ABSTRACT

A step h is provided between a recording region 2 including servo patterns Ps1, Ps2 and the recording track pattern Pw and a non-recording region 3 except the servo patterns Ps1, Ps2 and the recording track pattern Pw. A relation between a servo pattern width Ts and a track pitch Tp is set to be $Tp(n-0.1) \leq Ts \leq Tp(n+1)$, while a relation between a magnetic readout width Wr of the magnetic head and the track pitch Tp is set to be $0.9 Tp \leq Wr \leq 1.1 Tp$. A dead zone in a tracking error signal indicating a position of a magnetic head is to be eliminated, thus rendering it possible to position the magnetic head accurately and speedily.

20 Claims, 17 Drawing Sheets

Ps1, Ps2, Pw : RECORDING REGION 2

MAGNETIC DISK UNIT

This is a continuation of application Ser. No. 08/126,456 filed on Sep. 24, 1993, now abandoned.

FIELD OF THE INVENTION

This invention relates to a magnetic disc unit. More particularly, the invention relates to a magnetic disk unit with a magnetic recording medium having a step between a recording area and a non-recording area.

BACKGROUND

A magnetic disc unit using a magnetic disc is conventionally known. The magnetic disc, which may be a flexible disc or a hard disc, is loaded into the unit for recording or reproducing information signals on a uniform magnetic layer which is formed on the magnetic disc. Recording and reproduction are carried out with a magnetic head forming part of the magnetic disc unit. The magnetic head is positioned by a sector servo mode to carry out tracking adjustment.

FIG. 13A illustrates the sector servo mode with respect to a magnetic disc 101 controlled in rotation by the so-called CAV (constant angular velocity) mode. Each sector region as a unit for data recording is spatially divided into a servo region Zs and a data region Zd. The servo region Zs is usually arranged at the top of the sector region.

The servo region Zs has a servo pattern Ps arranged in a zigzag pattern with respect to the center of the track as shown in FIG. 13B. In this example, two servo patterns Ps1 and Ps2 are arranged in the zigzag pattern in each sector. Each of the servo patterns Ps1 and Ps2 has a larger width Ts (width always being defined as the direction of diameter of the disc) than the width Tw of a recording track pattern Pw in the data region Zd. Thus, one servo pattern is used for two adjacent tracks. An expanded diagram of each of the servo patterns Ps1 and Ps2 is shown in FIG. 13B. A magnetic domain having both magnetization directions is used as a unit. The magnetic domains are magnetized in the direction of the track. The magnetic readout width Wr of a magnetic head H is set to be substantially the same as the width Tw of the recording track pattern Pw. Accordingly, the magnetic readout width Wr is smaller than the width Ts of the servo patterns Ps1 and Ps2.

Next, positioning control of the magnetic head H based on the two servo patterns Ps1 and Ps2 in one sector is explained. When the magnetic head H traces the third track from the left and is positioned slightly toward the left side of the center of the third track as shown in FIG. 13B, an output level S1 of a reproduction signal passing the first servo pattern Ps1 is smaller than an output level S2 of the reproduction signal passing the second servo pattern Ps2. The relative output levels are shown in FIG. 14. This phenomenon is caused by the fact that a transit area of a gap in the magnetic head H is larger in the second servo pattern Ps2. By comparing the output levels S1 and S2 of the reproduction signal, how far the position of the magnetic head is shifted from the center of the track can be determined.

Specifically, the first reproduction signal S1 is produced when the head passes by the first servo pattern Ps1. This signal S1 is delayed for a predetermined period by a delay circuit. The delayed version of signal S1 is compared with the second reproduction signal S2 which is produced when the head passes by the second servo pattern Ps2. The two signals are compared by a differential amplifier. The output of the differential amplifier produces a tracking error signal St which can be used to determine the position of the magnetic head H. The tracking error signal St is supplied to a servo circuit for controlling the magnetic head H. A tracking actuator is connected to the servo circuit and is driven by the servo circuit. Thus, the position of the center of the magnetic head H is adjusted to follow the center of the track.

The conventional magnetic disc 101 is provided with a guard band between tracks for avoiding crosstalk from the adjacent track. Consequently, the track pitch Tp of the magnetic disc is larger than the width of the magnetic head H (the magnetic readout width Wr or the magnetic writing width Ww) in the conventional magnetic disc unit. In general, the ratio Wr/Tp of the magnetic readout width Wr and the track pitch Tp, and the ratio Ww/Tp of the magnetic writing width Ww and the track pitch Tp is not more than about 0.8 for securing good S/N in the conventional magnetic disc unit.

The output characteristics of the tracking error signal St are explained by reference to FIG. 15 in the case of the magnetic head H tracing an arbitrary position along the center of the track. The axis of ordinate represents the output level of the tracking error signal St from the differential amplifier and the axis of abscissas represents the position of the magnetic head H along the direction of diameter of the magnetic disc. As seen from the graph, when the magnetic head H passes the center of the track Tc, the output level of the error signal St is 0. The output level of the error signal St shifts to a positive or negative level as the magnetic head H shifts from the center of the track Tc. However the ratio Wr/Tp and the ratio Ww/Tp are not more than about 0.8, and Wr is set to be smaller than Ts in the conventional case. Therefore the magnetic head H happens to trace within either servo pattern Ps1 or Ps2. The error signal St is substantially constant when the magnetic head traces within either the pattern Ps1 or Ps2. That is, there is a dead zone in which the level of the tracking error signal St does not change despite the change of the position of the magnetic head H in the conventional case. This phenomenon also occurs when the track pitch Tp and the width Ts of the servo pattern Ps1 or Ps2 are substantially the same, as shown in FIG. 16. Thus, a dead zone in the signal is generated, indicating that the error signal St is substantially constant between when one end (the left end in the drawing) of the magnetic head H is positioned on one end (the left end in the drawing) of the first sample servo Ps1, and a state in which the other end (the right end in the drawing) of the magnetic head H is positioned on the other end (the right end in the drawing) of the sample servo Ps1.

Accordingly, the position of the magnetic head H cannot be correctly determined when the magnetic head traces on the dead zone. This causes the problem that the magnetic head H doesn't move to the correct position (in the direction of diameter) when the magnetic head either reproduces data of a demanded address (sector) or writes data in the address (sector). That is, step jump operation, track jump operation and seek operation cannot be carried out accurately. This causes long delays in accessing data.

When the magnetic readout width Wr is substantially the same as the width Ts of the servo pattern and is smaller than the track pitch Tp as shown in FIG. 17A, the change of the signal is small even though the dead zone is improved as shown in FIG. 17B. Therefore, when the magnetic head passes the dead zone, the servo gain becomes extremely small and the magnetic head isn't positioned accurately by the servo circuit.

Thus, it is desirable to eliminate the dead zone in order to position the magnetic head H more accurately and speedily. In addition, since the relation between the magnetic readout width Wr, the magnetic writing width Ww and the width Tw of the recording track pattern Pw is approximately Wr=Ww=Tw in the conventional magnetic disc unit, when the magnetic head is off the track from the recording track pattern Pw even slightly at the time of reproduction, the output is lower than if the head is on the track as shown in FIG. 18A. If the magnetic head is off the track at the time of recording, a portion of the previously recorded information remains. This remaining information acts as noise at the time of reproduction. Thus, the overwrite S/N (signal to noise ratio) of the magnetic head is degraded. When the magnetic disc unit is vibrated, the problem of off tracking is generated more frequently. This limits the circumstances under which the magnetic disc unit can be used.

SUMMARY OF THE INVENTION

One object of this invention is to provide a magnetic disc unit whereby it is possible to position the magnetic head quickly and accurately.

Another object of this invention is to provide a magnetic disc unit whereby it is possible to carry out recording and reproduction even when the magnetic disc unit is vibrated without excessive degradation of the S/N ratio.

These and other objects, advantages and features of the invention will become apparent to those skilled in the art upon consideration of the following description of the invention.

According to the present invention, there is provided a magnetic disc unit employing a magnetic recording medium having a servo region Zs and a data region Zd alternately allocated. The servo region Zs has a servo pattern Ps (Ps1 and Ps2) with a servo pattern width Ts. The data region Zd has a recording track pattern Pw with a track pitch Tp and a recording track width Tw. The recording medium has a step h between a recording region including the servo pattern Ps and the recording track pattern Pw and a non-recording region. The magnetic disc unit employs a magnetic head H with a magnetic writing width of Ww and a magnetic readout width Wr. The magnetic readout width Wr of the magnetic head H is substantially equivalent to the track pitch Tp. The servo pattern width Ts is substantially equivalent to the track pitch Tp or an integer multiple thereof.

In another aspect of the invention a magnetic disc for use in a magnetic disc unit having a magnetic head with a magnetic writing width of Ww and a magnetic readout width of Wr includes a magnetic recording medium having a servo region and a data region alternately allocated, the servo region having a servo pattern with a servo pattern width Ts, the data region having a recording track pattern with a track pitch Tp and a recording track width Tw, and having a step between a recording area and a non-recording area thereon. The track pitch Tp is substantially equivalent to the magnetic readout width Wr. The servo pattern width Ts is substantially equivalent to the track pitch Tp or an integer multiple thereof.

The features of the invention believed to be novel are set forth with particularity in the appended claims. The invention itself however, both as to organization and method of operation, together with further objects and advantages thereof, may be best understood by reference to the following description taken in conjunction with the accompanying drawing.

BRIEF DESCRIPTION OF THE DRAWINGS

FIG. 1 is made up of FIG. 1A showing a track format thereof, and FIG. 1B showing a servo pattern and a pattern arrangement in the vicinity of the servo pattern.

FIG. 2 is made up of FIG. 2A which is a plan view showing the servo pattern and the pattern arrangement in the vicinity thereof, and FIG. 2B which is a cross-sectional view on a line A—A shown in FIG. 2A.

FIG. 3 is made up of FIG. 3A, which is a plan view showing the servo pattern and the pattern arrangement in the vicinity thereof, and FIG. 3B which is a cross-sectional view on a line B—B shown in FIG. 3A.

FIG. 4 includes FIG. 4A and FIG. 4B. FIG. 4A is a plan view showing the servo pattern and the pattern arrangement in the vicinity thereof. FIG. 4B is a cross-sectional view on a line C—C shown in FIG. 4A.

FIG. 5 is a diagram showing a state of magnetization of essential portions of the magnetic disc corresponding to FIG. 3. FIG. 5 is made up of FIG. 5A and FIG. 5B.

FIG. 6, made up of FIG. 6A and FIG. 6B, shows the magnetic head tracing an arbitrary position on the magnetic disc used in the magnetic disc unit of the present invention.

FIG. 7, made up of FIG. 7A and FIG. 7B, shows the magnetic head tracing an arbitrary position on the magnetic disc used in the magnetic disc unit of the present invention.

FIG. 8 is made up of FIG. 8A which shows the range at the time of reproduction, and FIG. 8B which shows the range at the time of recording.

FIG. 11 is made up of FIG. 11A which is a plan view thereof, and FIG. 11B which is a waveform diagram showing the change in the output level of the tracking error signal corresponding to the change in the position of the magnetic head along diameter of the magnetic disc. FIG. 12 is made up of FIG. 12A and FIG. 12B. FIG. 12A is a plan view thereof, and FIG. 12B is a waveform diagram showing the change in the output level of the tracking error signal corresponding to the change in the position of the magnetic head along diameter of the magnetic disc.

FIG. 13 is made up of FIG. 13A which shows a track format thereof, and FIG. 13B which shows a servo pattern and a pattern arrangement in the vicinity thereof.

FIG. 16, which is made up of FIG. 16A and FIG. 16B, shows the magnetic head traces an arbitrary position on the magnetic disc used in the magnetic disc unit according to the conventional example.

FIG. 17, which is made up of FIG. 17A and FIG. 17B, shows the magnetic head traces an arbitrary position on the magnetic disc used in the magnetic disc unit according to another conventional example.

FIG. 18 is made up of FIG. 18A, which shows the state at the time of reproduction and FIG. 18B, which shows the state at the time of recording.

DESCRIPTION OF THE INVENTION

Figure 1A:
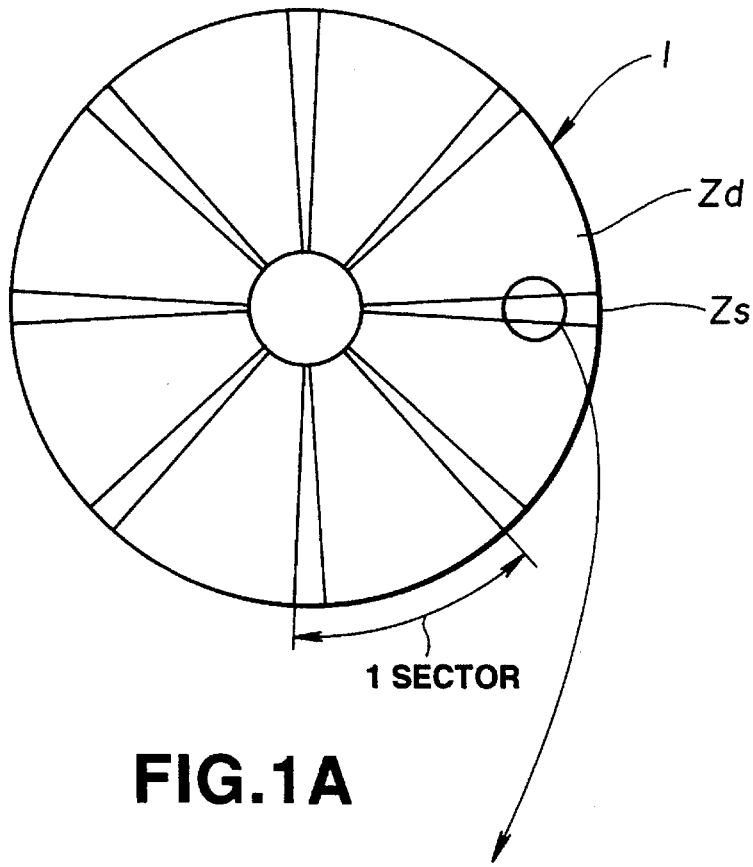
FIG. 1 is a diagram showing an arrangement of a magnetic disc used in a magnetic disc unit of the present invention.

While this invention is susceptible of embodiment in many different forms, there is shown in the drawings and will herein be described in detail specific embodiments, with the understanding that the present disclosure is to be considered as an example of the principles of the invention and not intended to limit the invention to the specific embodiments shown and described. In the description below, like reference numerals are used to describe the same, similar corresponding parts in the several views of the drawing.

A preferred embodiment of the magnetic disc unit of the present invention is explained hereinbelow, with reference to FIGS. 1 to 12. An arrangement of a magnetic recording medium (referred to as a magnetic disc hereinafter) used in the magnetic disc unit of the present embodiment is first explained on the basis of FIGS. 1 to 5.

The magnetic disc is controlled in rotation in, for example, the CAV (constant angular velocity) mode as shown in FIG. 1A. The magnetic disc has sector regions as a unit for data recording. Each sector region is spatially divided into a servo region Zs and a data region Zd. The servo region Zs is arranged at the top of the sector region. Since the magnetic disc is controlled in rotation in the CAV mode, the servo region Zs and the data region Zd are arranged radially and alternately in the form of track format.

Figure 1B:
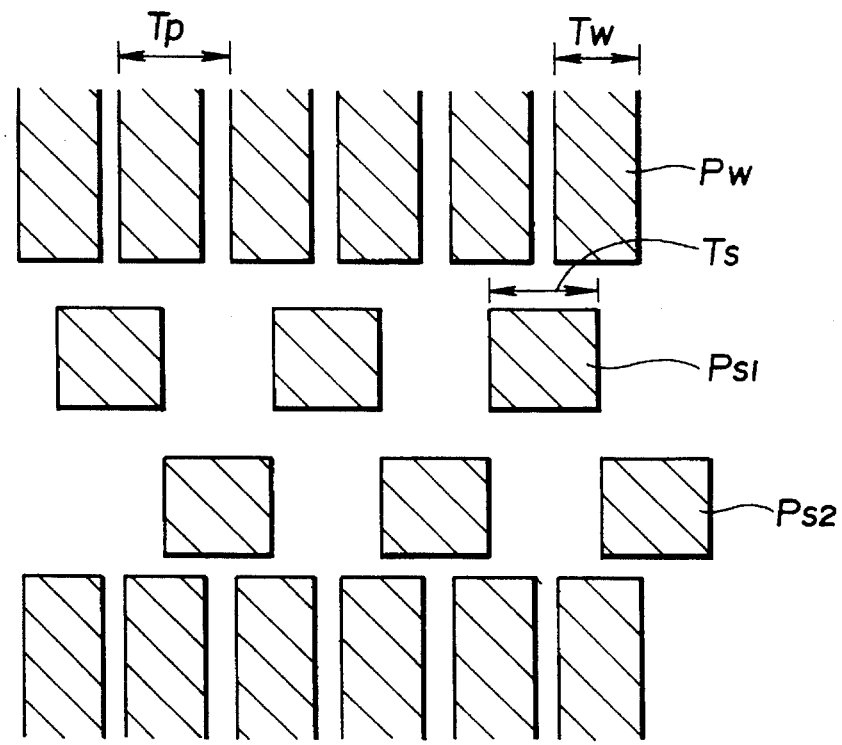

As shown in FIG. 1B, plural servo patterns Ps1 and Ps2 having a servo pattern width Ts are arranged and formed in a zigzag pattern along the center of the track in the servo region Zs. A recording track pattern Pw having a track pitch Tp and a recording track width Tw is formed in the data region Zd.

Figure 2A:
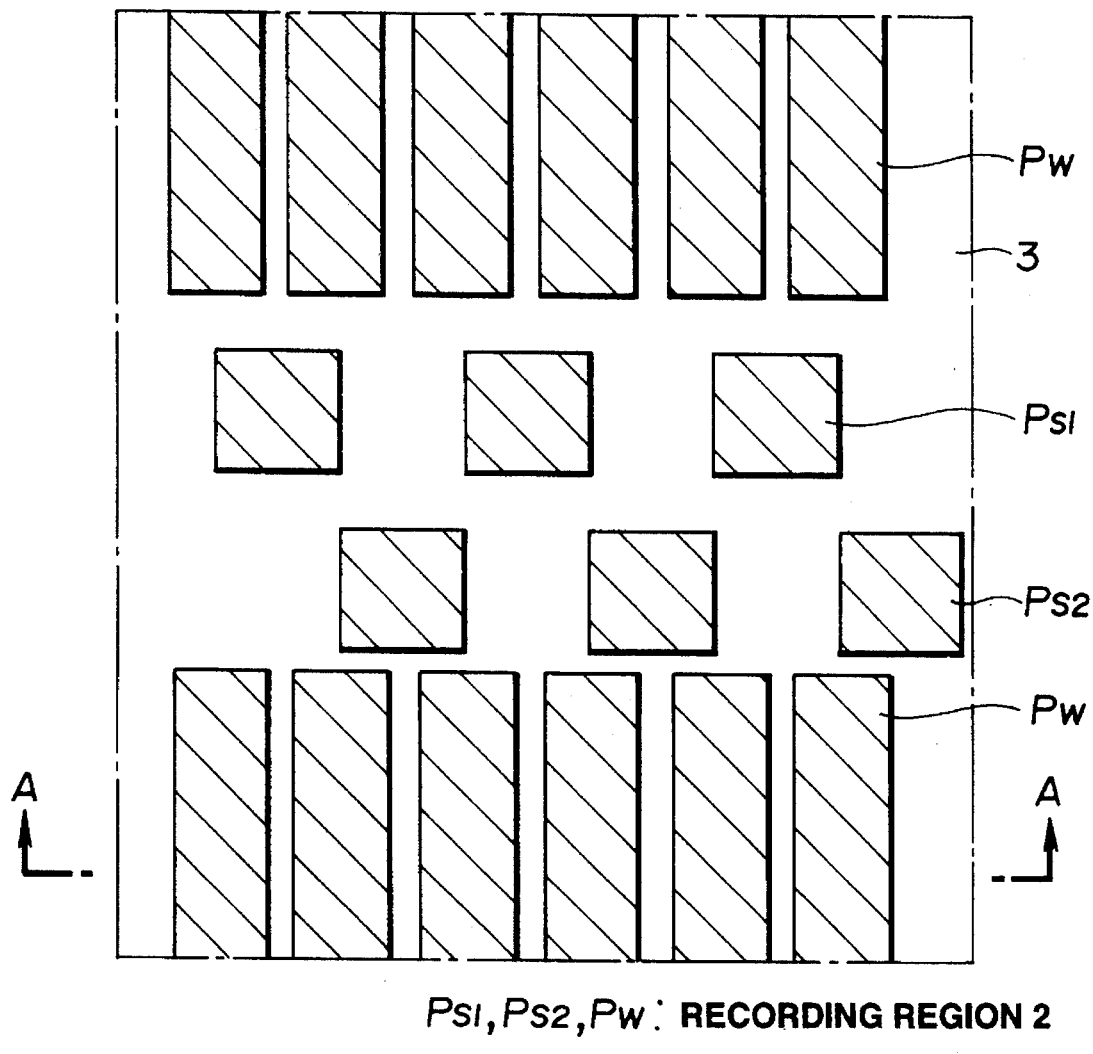
FIG. 2 is a diagram showing an arrangement of essential portions of the magnetic disc used in the magnetic disc unit of the present invention.
Figure 2B:
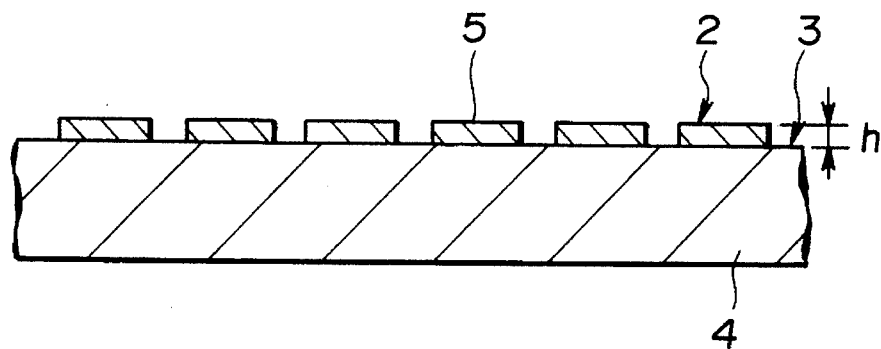

A step h is provided between a recording area 2 including the servo patterns Ps1, Ps2 and the recording track pattern Pw and a non-recording area 3 except the servo patterns Ps1, Ps2 and the recording track pattern Pw, as shown in FIG. 2A and FIG. 2B. That is, the recording track pattern Pw and the servo patterns Ps1, Ps2 are formed by partly changing magnetic characteristics of the magnetic disc 1 observed from the magnetic head.

The servo patterns Ps1, Ps2 and the recording track pattern Pw is formed as follows. A magnetic film 5 is formed on the entire surface of a disc substrate 4 and then undesired portions of the magnetic film 5 is removed by an etching technique. This leaves a step h of thickness equal to the thickness of the magnetic film.

Figure 3A:
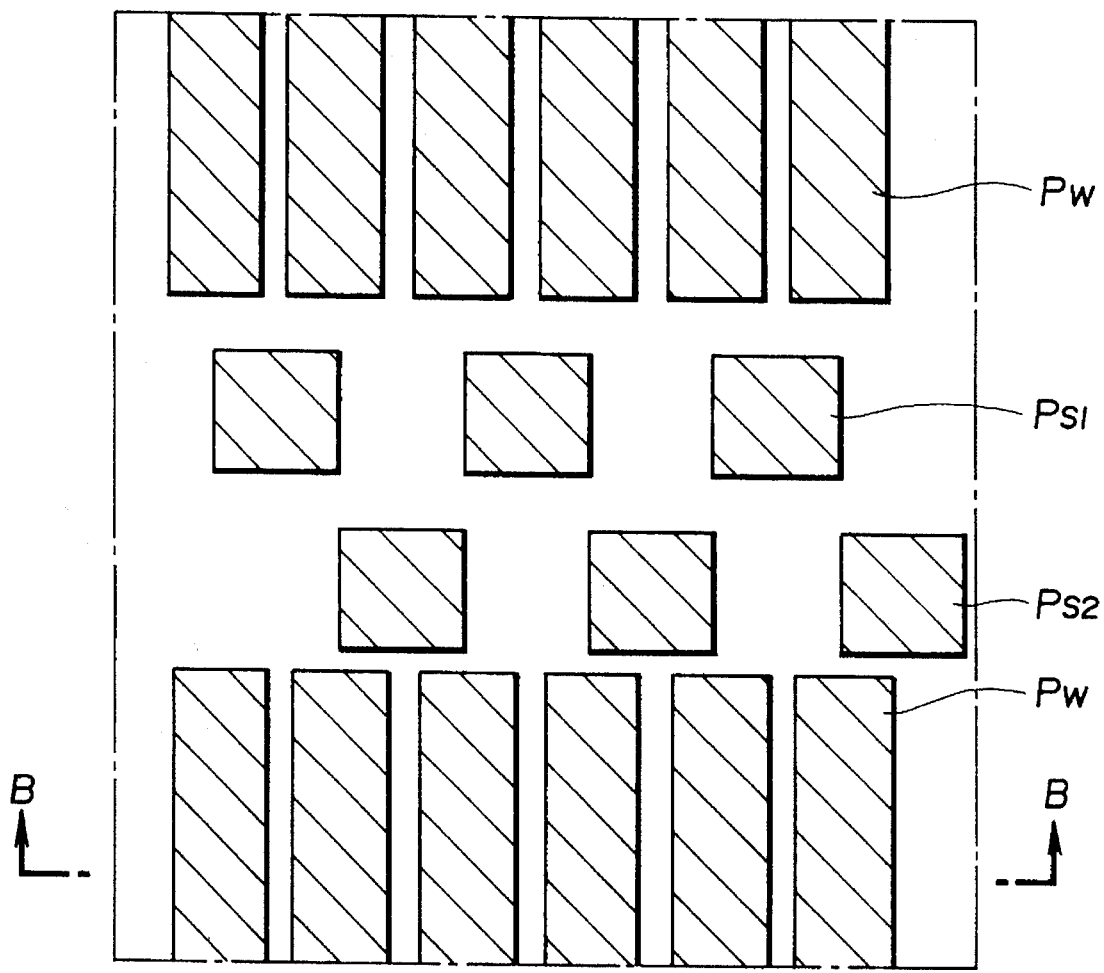
FIG. 3 is a diagram showing another arrangement of essential portions of the magnetic disc used in the magnetic disc unit of the present invention.
Figure 3B:
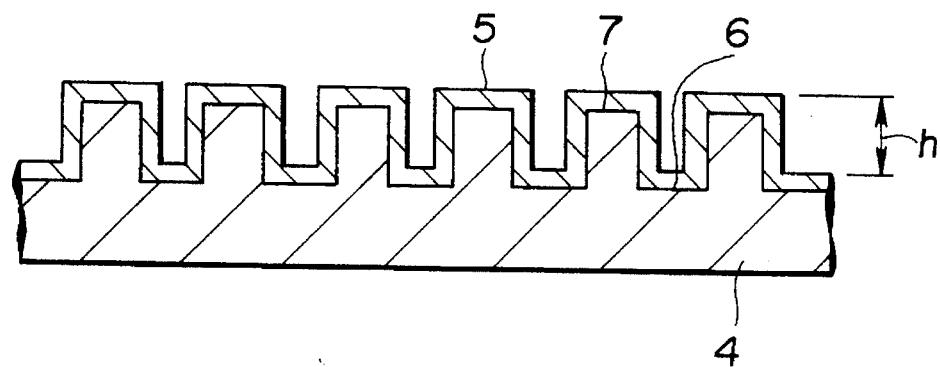

The servo patterns Ps1, Ps2 and the recording track pattern Pw of another example as shown in FIG. 3B is formed as follows. A recess 6 and a projection 7 corresponding to the servo patterns Ps1, Ps2 and the recording track pattern Pw are formed on the surface of the disc substrate 4 by a mechanical processing technique such as molding or machining or chemical processing technique such as etching, and then the magnetic film 5 is formed on the entire surface of the substrate 4. Then, the servo patterns Ps1 and Ps2 are magnetized in one direction to complete the magnetic disc.

Figure 4:
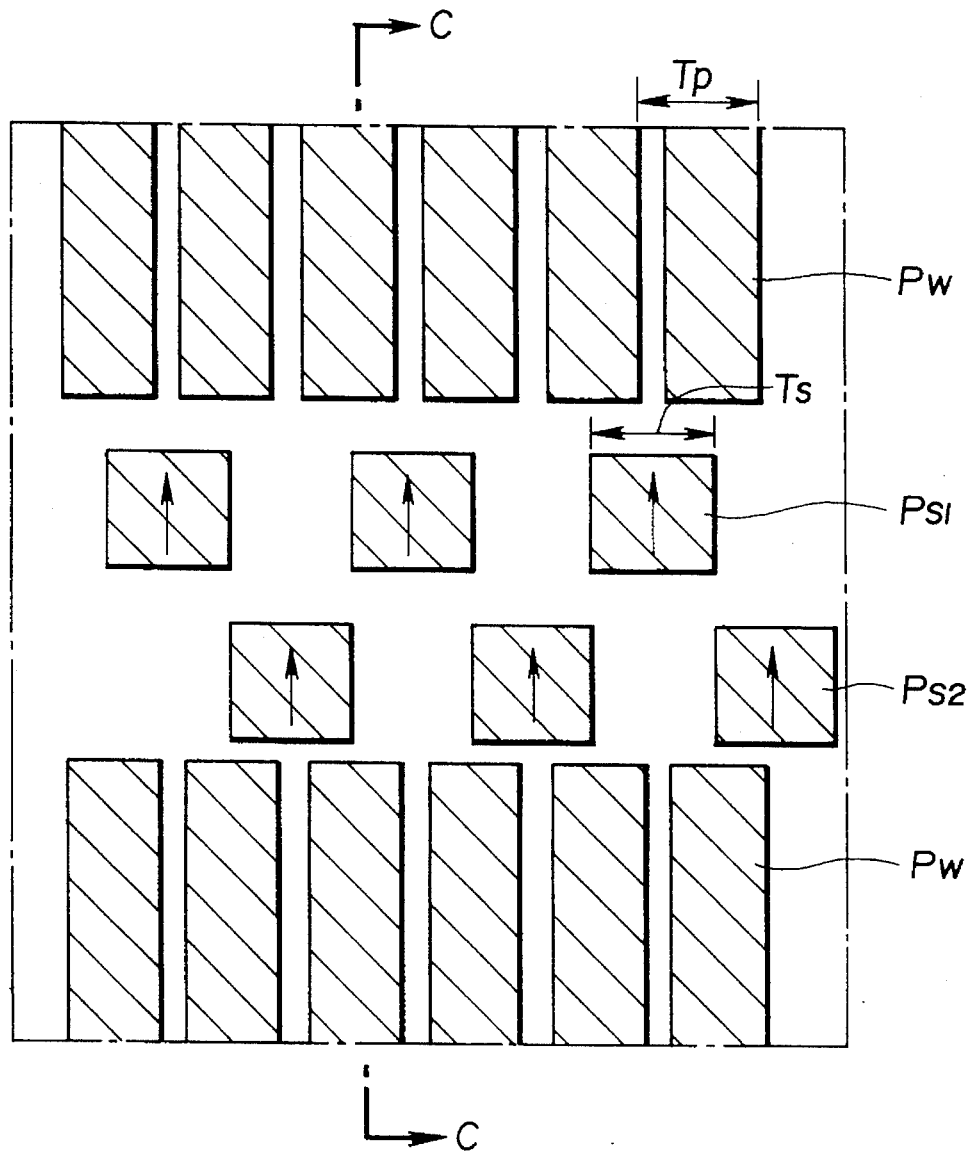
FIG. 4 is a diagram showing a state of magnetization of essential portions of the magnetic disc corresponding to FIG. 2.
Figure 4:
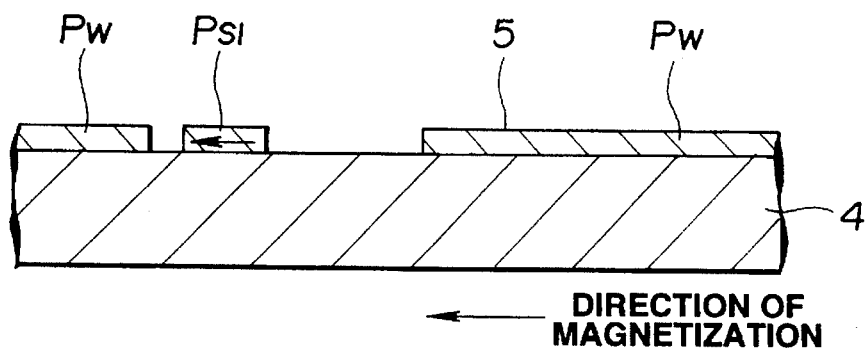
Figure 5A:
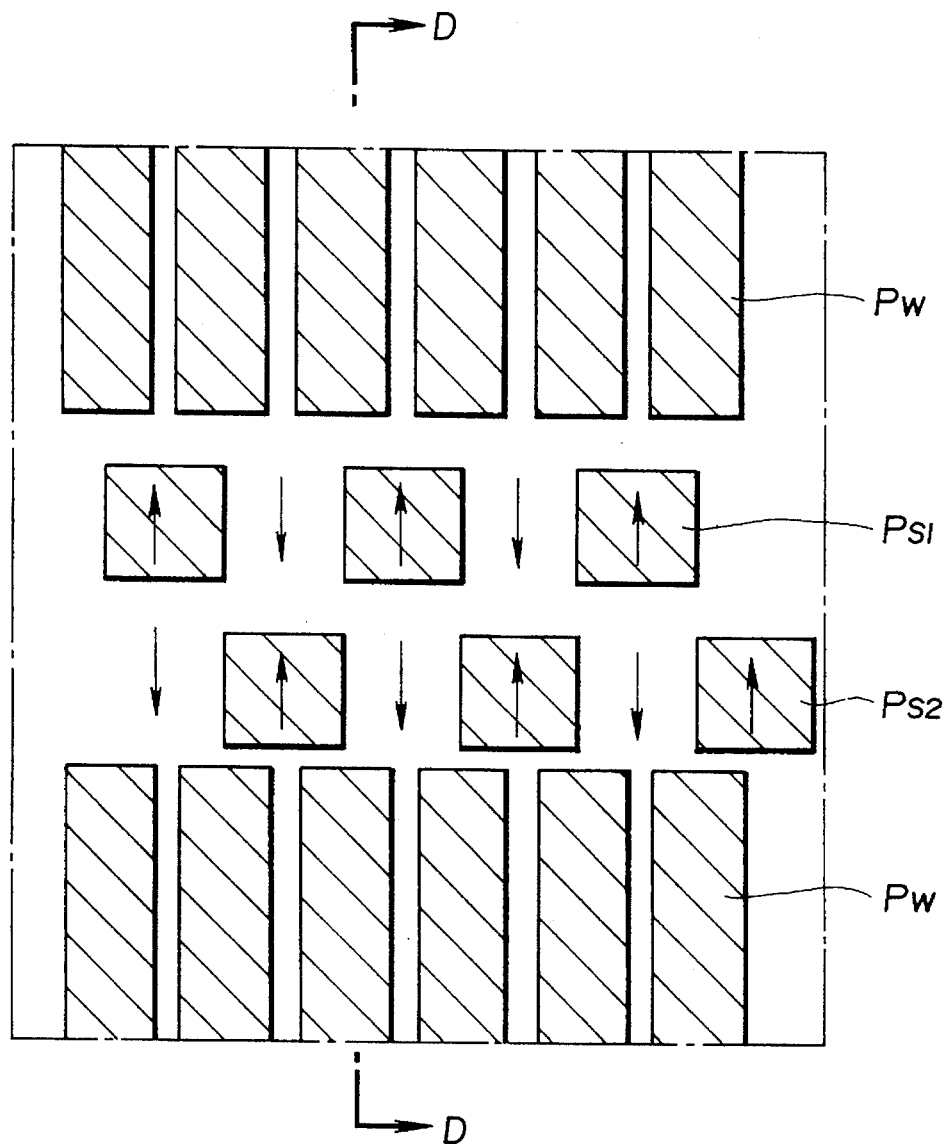
FIG. 5A is a plan view showing the servo pattern and the pattern arrangement in the vicinity thereof.
Figure 5B:
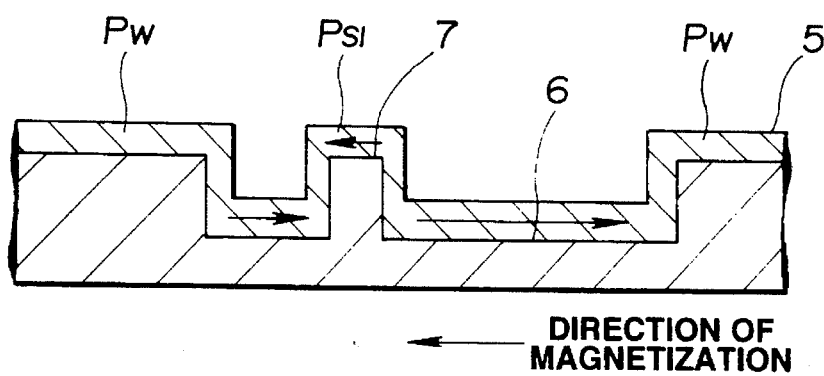
FIG. 5B is a cross-sectional view on a line D—D shown in FIG. 5A.

As a method of magnetization, the substrate from which the magnetic film 5 has been removed as shown in FIG. 2B is magnetized by a magnetic head through which a direct current is run, in the direction shown in FIG. 4. As for the disc substrate 4 having the recess and projection on which the magnetic film 5 is formed as shown in FIG. 3B, the magnetic film 5 on the recess 6 and the projection 7 may be magnetized in the first direction by a magnetic head through which a current Ib is run, and then the magnetic film 5 on the projection 7 may be magnetized in the opposite direction to the first direction with a current −Iu (Ib>Iu). Otherwise, while the rotation of the magnetic disc is slowed down to diminish the distance between the magnetic head and the surface of the magnetic disc, the magnetic film 5 on the recess 6 and the projection 7 is magnetized in the first direction. While the rotation of the magnetic disc 1 is accelerated to increase the distance between the magnetic head and the surface of the magnetic disc, the magnetic film 5 on the projection 7 is magnetized in the opposite direction to the first direction.

Figure 6A:
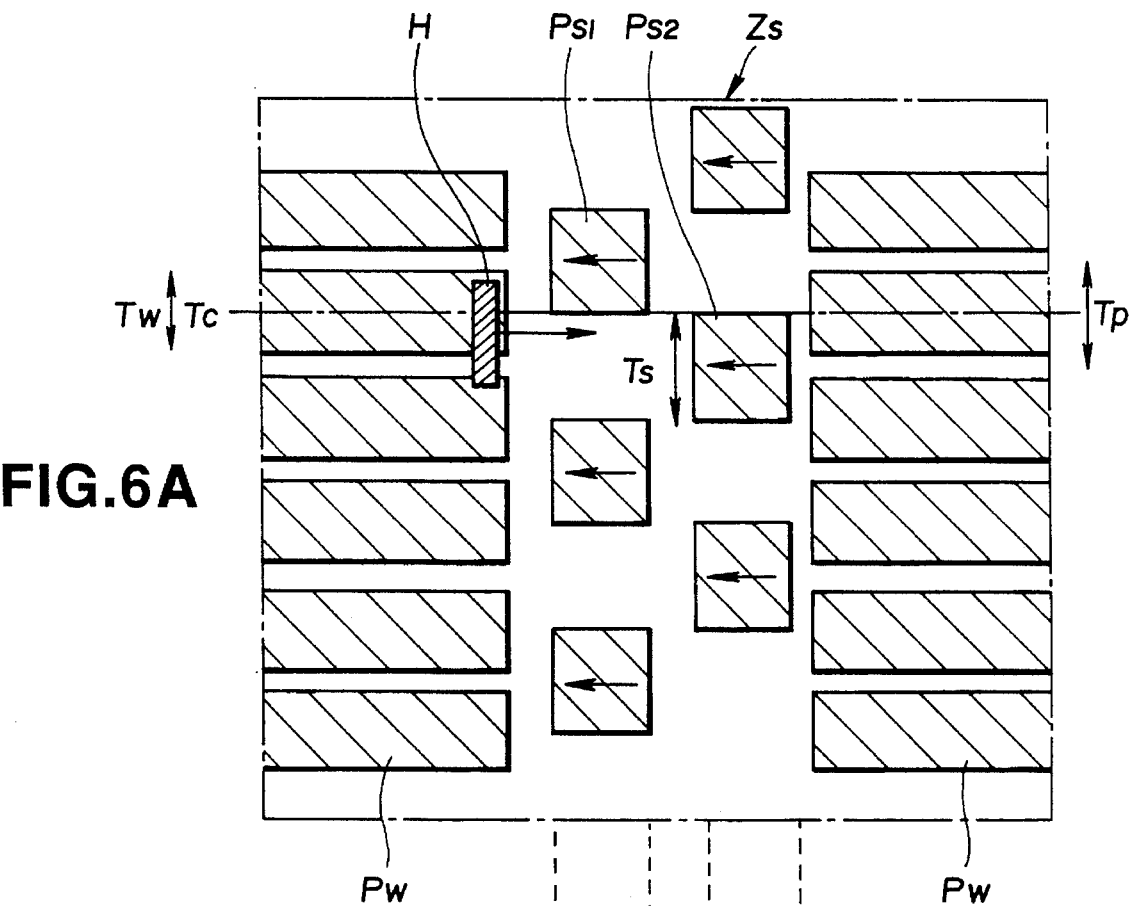
FIG. 6A is a plan view thereof.
Figure 6B:
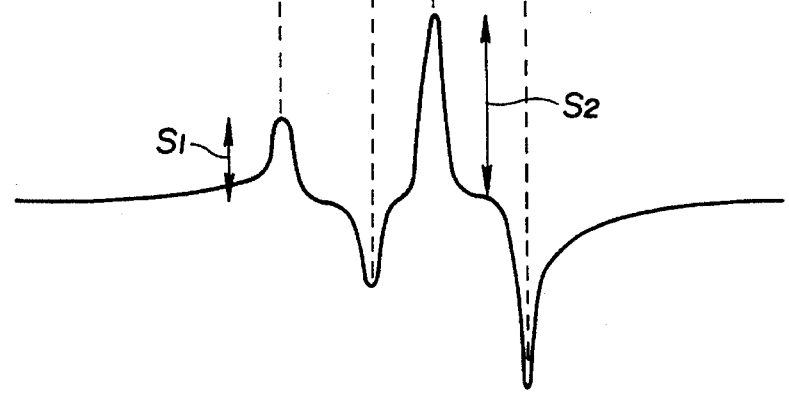
FIG. 6B is a waveform diagram showing a detection signal from the magnetic head.

When the magnetic head traces on the servo region Zs in which the two servo patterns Ps1 and Ps2 are arranged in a zigzag pattern with respect to the center of the track Tc as shown in FIG. 6A, a reproduction signal is a signal waveform having a peak on the boundary where the magnetization direction reverses, as shown in FIG. 6B. Particularly in the example of FIG. 6A, since the magnetic head traces the portion toward the second servo pattern Ps2 with respect to the center of the track, the output level (peak value S1) of the reproduction signal (detection signal) on the first servo pattern Ps1 is smaller than the output level (peak value S2) of the reproduction signal (detection signal) of the second servo pattern Ps2.

The distance the magnetic head is shifted from the center of the track Tc can be determined by the difference between the output levels S1 and S2. Consequently, it is possible to have the center of the magnetic head follow the center of the track, by supplying the signal (tracking error signal) St indicating the difference between the output levels S1 and S2 to a servo circuit for servo-controlling the magnetic head and then driving a tracking actuator connected to the servo circuit. As the magnetic head used in the magnetic disc unit, various types of heads can be used, such as, a winding type bulk head, an inductive type thin film head, and a composite thin film head combining an inductive type recording head and a magnetic resistance effect reproduction head.

The magnetic readout width Wr of the magnetic head and the width Ts of the servo patterns Ps1, Ps2 are so set as to satisfy conditions indicated by the following Formula 1.

$$Tp(1-dr) \leq Wr \leq Tp(1+dr)$$

$$Tp(n-ds) \leq Ts \leq Tp(n+ds) \quad \text{Formula 1}$$

In the above formula, n is a positive integer, indicating that the width Ts of the servo patterns Ps1, Ps2 is set to be n times as large as the track pitch Tp. The dr and ds are set to 0.1, which are constants expressing ratios of processing error of the magnetic readout width Wr and the servo pattern width Ts. With the present processing technique, the ratios of processing error dr, ds can be about 0.1.

Accordingly, when both of the ratios of processing error dr, ds are zero, a relation of the following Formula 2 holds.

$$Tp=Wr=(Ts/n) \quad \text{Formula 2}$$

When the center of the magnetic head traces on the center of track Tc, as shown in FIG. 7, the output level of the detection signal in one servo pattern Ps1 and in the other servo pattern Ps2 are equal. It causes the difference of the detection signals (the output level of the tracking error signal St) to be 0. When the magnetic head is shifted toward the other servo pattern Ps2, the output level in the servo pattern Ps2 becomes larger than that in the servo pattern Ps1. This causes the level corresponding to the shift as the difference between the detection signals. Particularly, when the magnetic head is positioned on the servo pattern Ps2, there is no detection of the signal by the servo pattern Ps1, thereby maximizing or minimizing the difference.

Figures 7A, 7B:
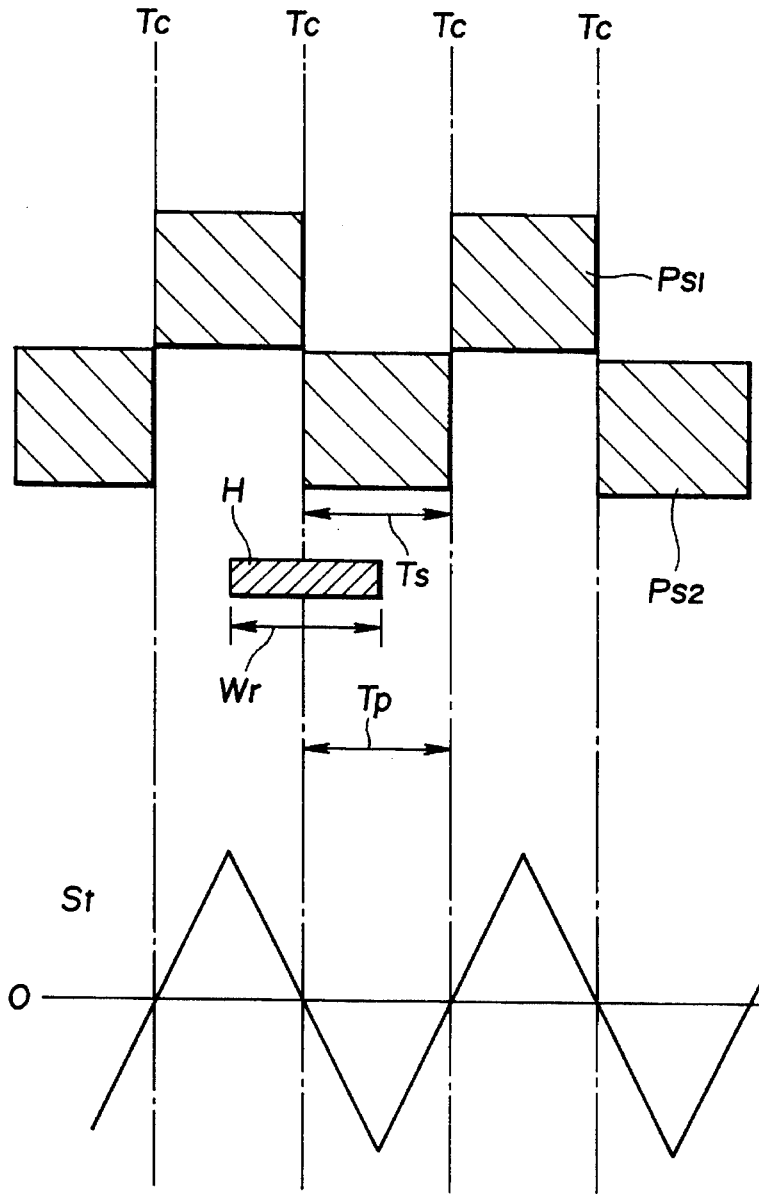
FIG. 7A is a plan view thereof.
FIG. 7B is a waveform diagram showing a change in an output level of a tracking error signal corresponding to a change in the position of the magnetic head along diameter of the magnetic disc.
Figure 8:
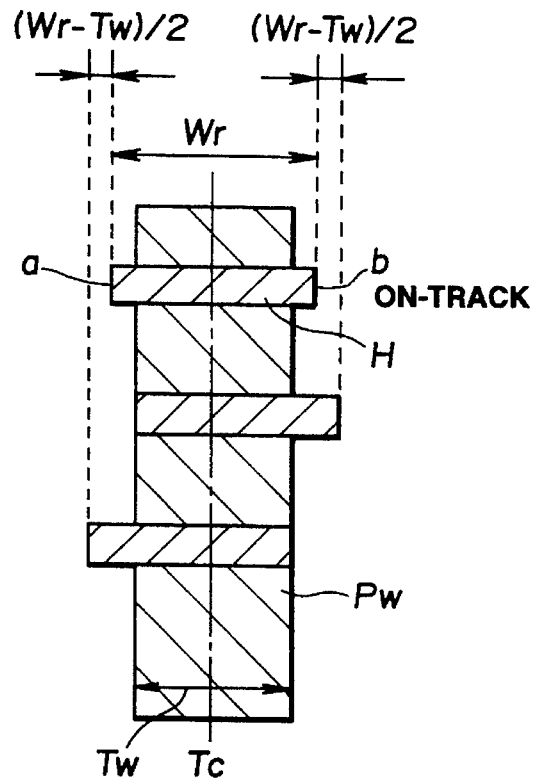
FIG. 8 shows an allowable range of off-tracking of the magnetic head of the magnetic disc unit according to the present invention.
Figure 8:
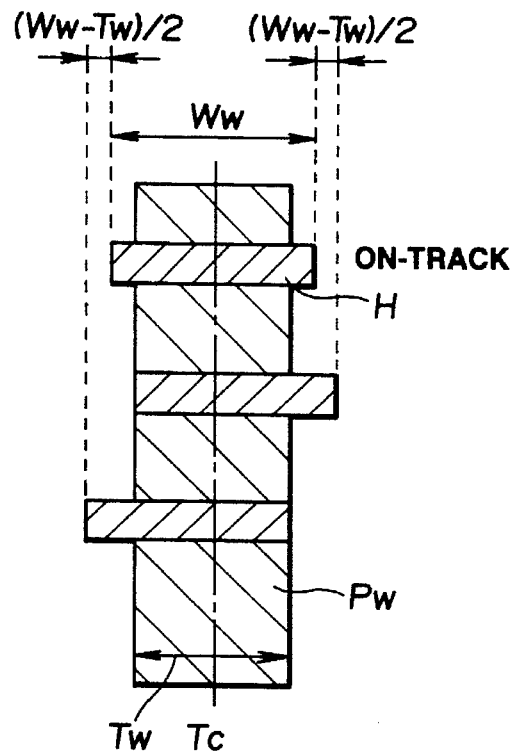
Figure 9:
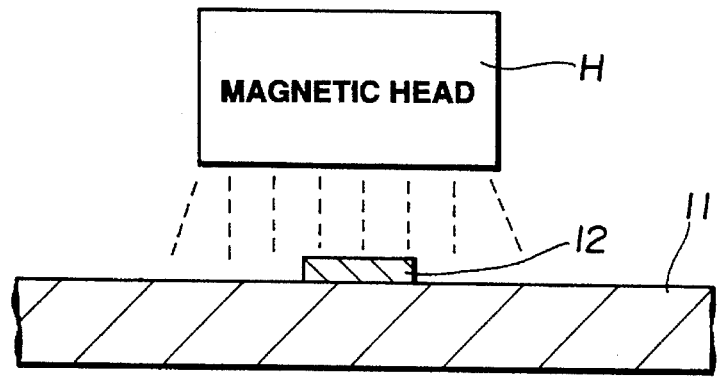
FIGS. 9A–9C show a method of measuring a magnetic readout width of the magnetic head of the magnetic disc unit of the present invention.
Figure 9:
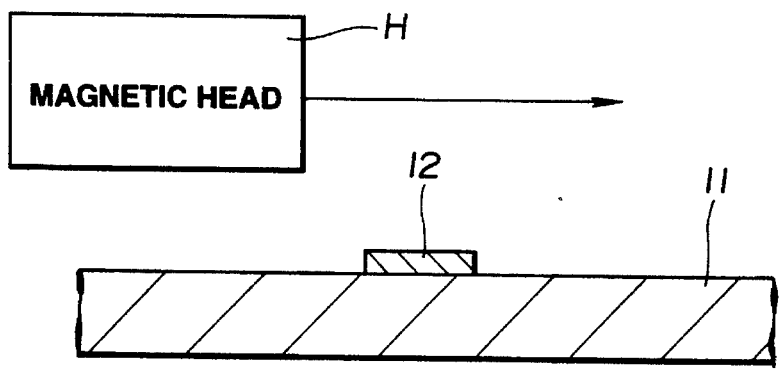
Figure 9:
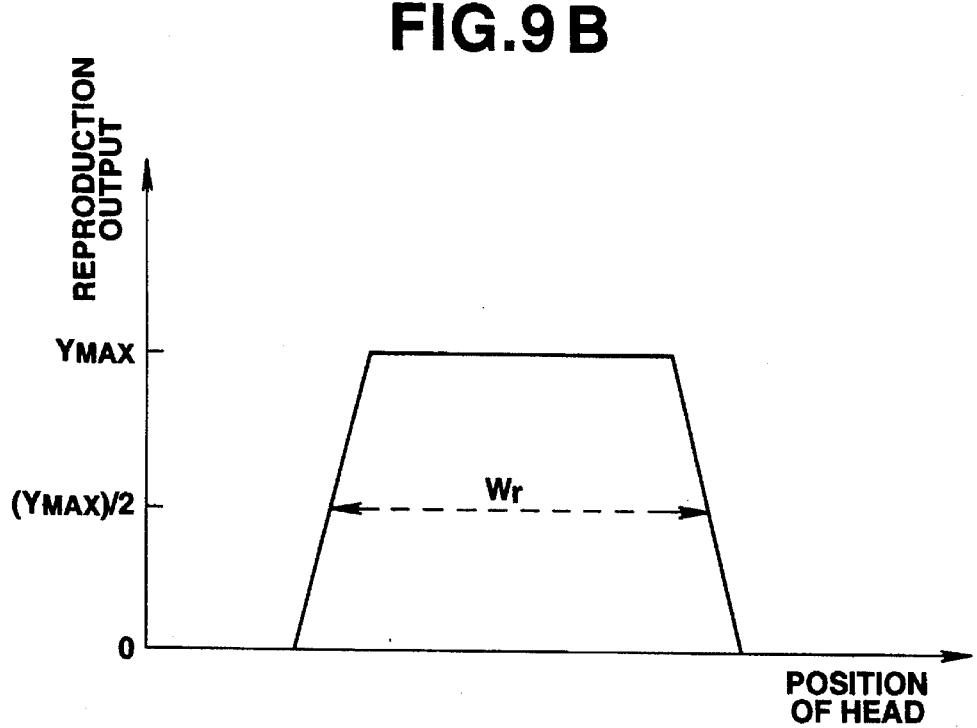

Even though the magnetic head is slightly shifted from this state toward the inner circle or the outer circle of the magnetic disc, the magnetic head detects the servo pattern Ps1. So, in the present invention there is no dead zone in the output level of the tracking error signal St. That is, the signal waveform of the tracking error signal St along the diameter of the magnetic disc has a linear characteristics from the minimum level to the maximum level without any dead zone, as shown in FIG. 7B.

The size of dead zones caused by the size of Tp, Ts/n, Wr accompanying the processing errors dr, ds is shown in Table 1.

From the above Table 1, it is found that the dead zone is always smaller than 0.2 Tp when the track pitch Tp, the servo track width Ts and the magnetic readout width satisfy the relation of the Formula 1.

Figure 13A:
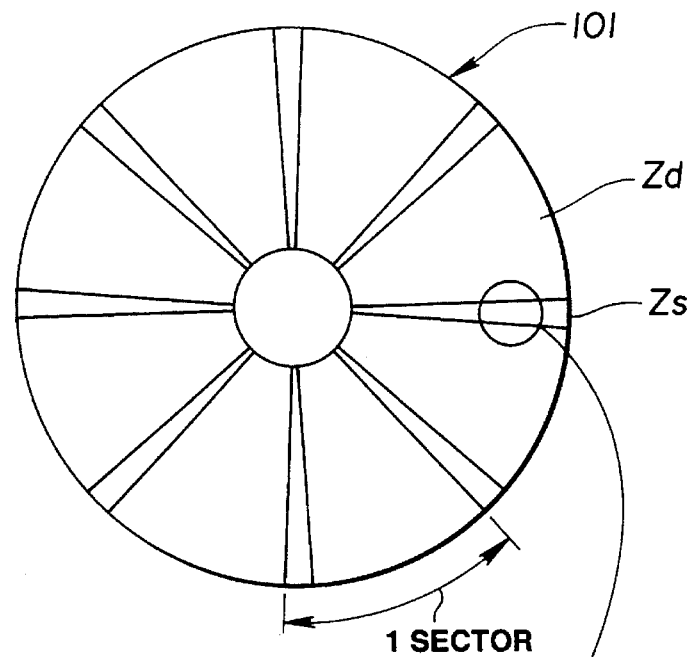
FIG. 13 shows an arrangement of a magnetic disc used in a magnetic disc unit according to a conventional example.
Figure 13B:
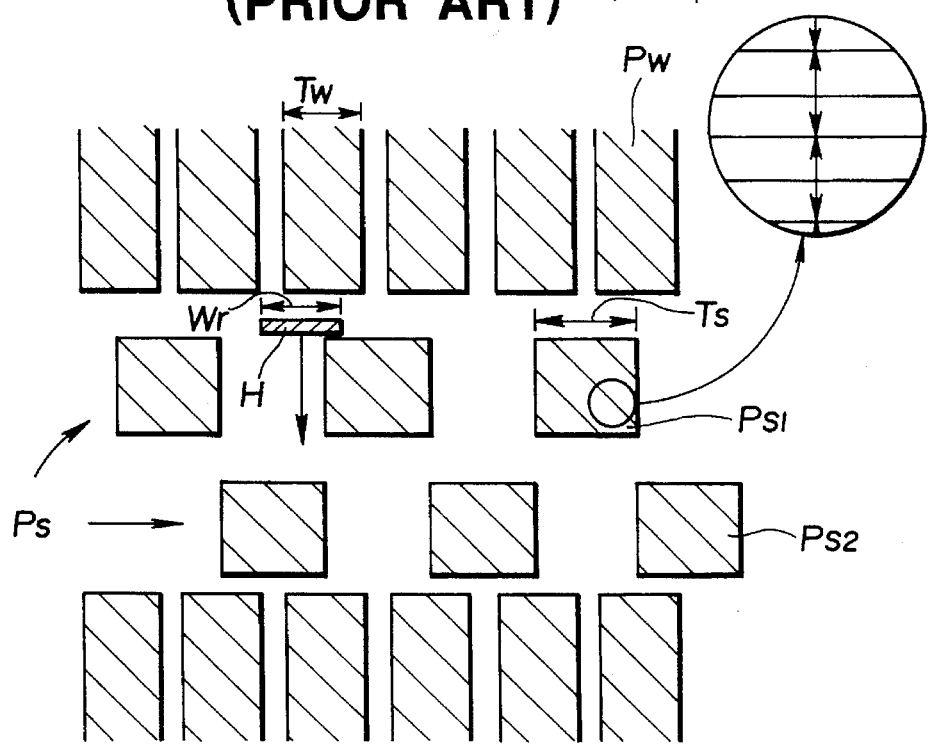
Figure 14:
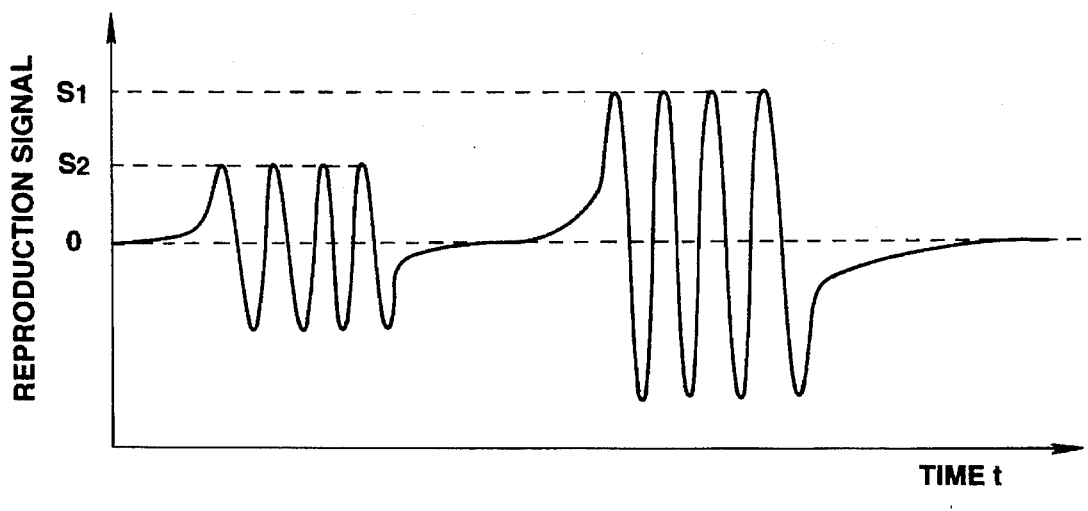
FIG. 14 is a waveform diagram showing a detection signal from a magnetic head at the time when the magnetic head traces an arbitrary position on the magnetic disc used in the magnetic disc unit according to the conventional example.
Figure 15:
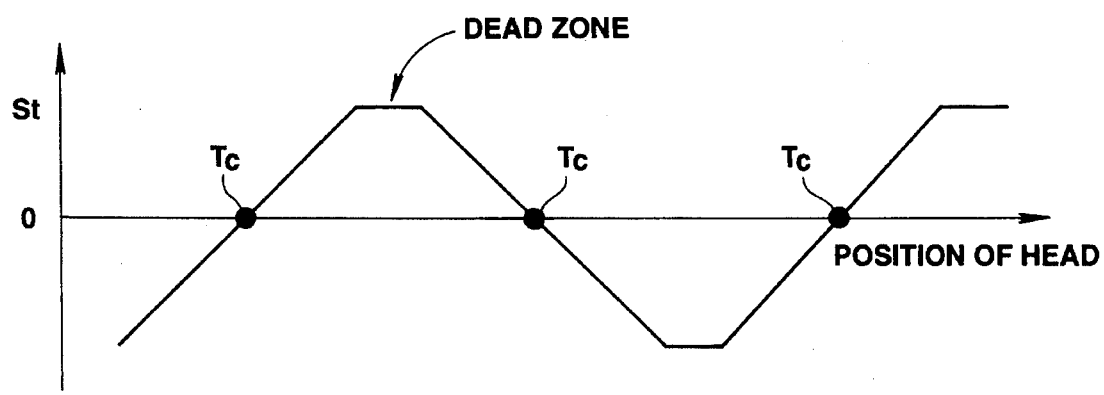
FIG. 15 is a waveform diagram showing a change in the output level of the tracking error signal corresponding to a change in the position of the magnetic head along the diameter of the magnetic disc according to the conventional example.
Figure 16A:
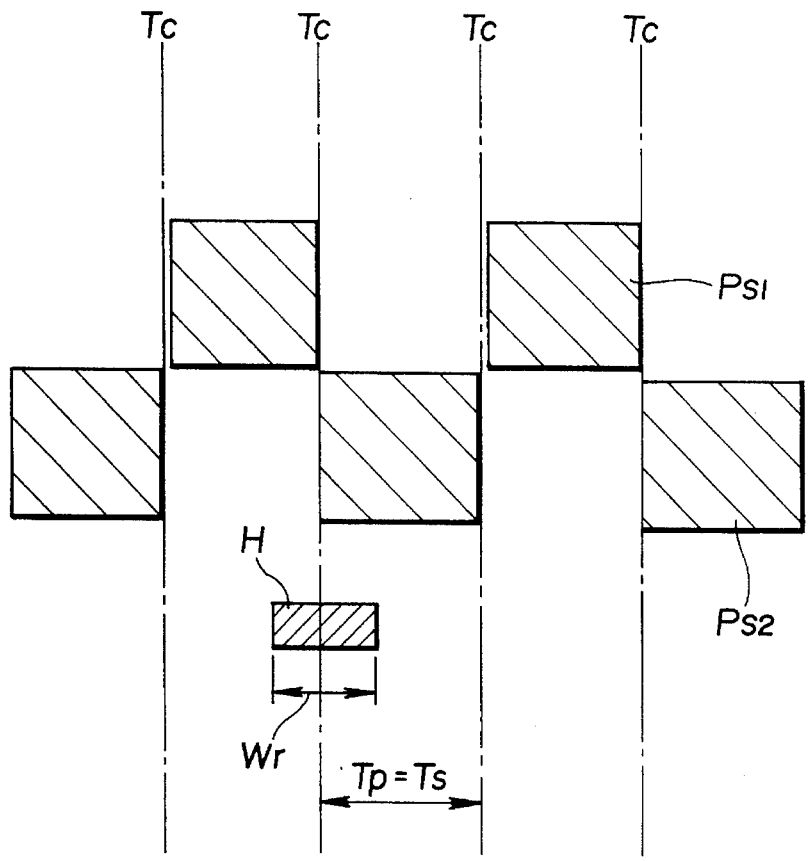
FIG. 16A is a plan view thereof.
Figure 16B:
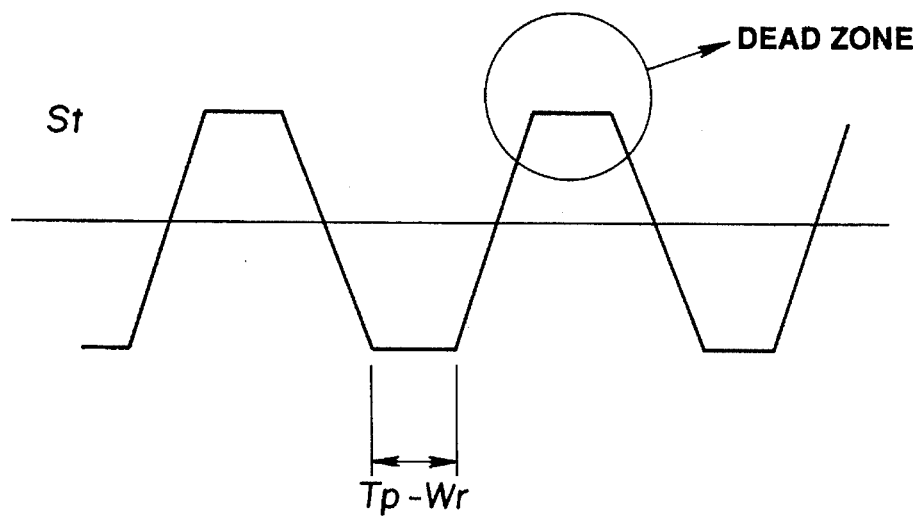
FIG. 16B is a waveform diagram showing the change in the output level of the tracking error signal corresponding to the change in the position of the magnetic head along the diameter of the magnetic disc.
Figure 17A:
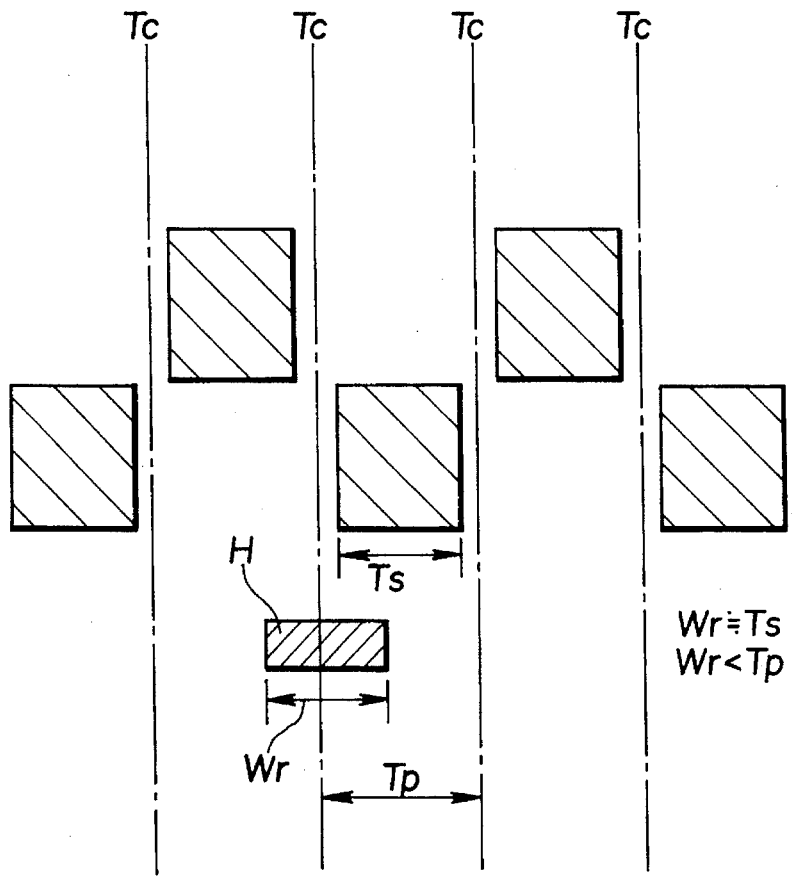
FIG. 17A is a plan view thereof.
Figure 17B:
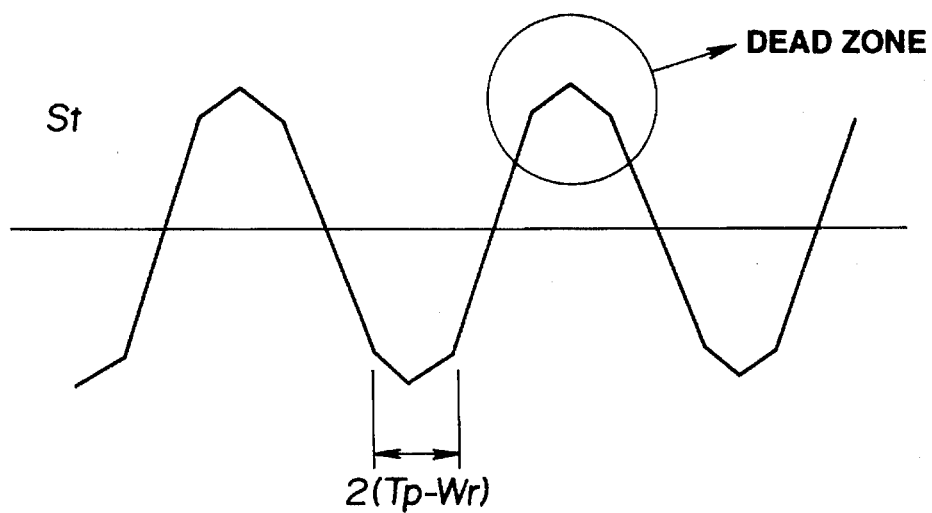
FIG. 17B is a waveform diagram showing the change in the output level of the tracking error signal corresponding to the change in the position of the magnetic head along the diameter of the magnetic disc.
Figure 18A:
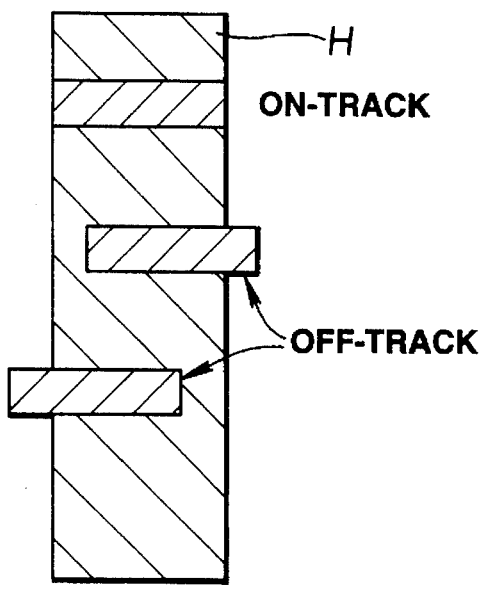
FIG. 18 is an explanatory view showing a state of off-tracking in the magnetic head of the magnetic disc unit of the conventional example.
Figure 18B:
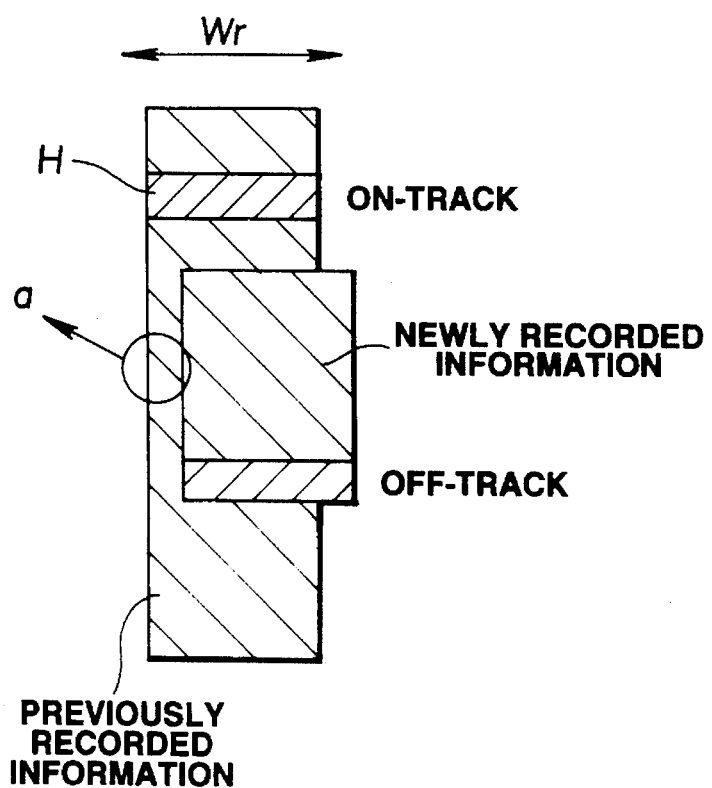

When the conventional magnetic disc shown in FIG. 13 is recorded and reproduced, the relation of the magnetic writing width Ww, the magnetic readout width Wr, the recording track width Tw and the track pitch Tp can only be Ww=Wr=Tw<Tp, not satisfying the condition indicated by Formula 1. The track pitch Tp and the magnetic readout width Wr in conventional magnetic disc units sold in the market were measured. The results are shown in Table 2. From the results of the measurement, it is expected that the size of the dead zone in the conventional magnetic disc unit is lager than 0.2 Tp.

TABLE 2

|  | Head Width Wr | Track Pitch Tp | Wr/Tp |
|---|---|---|---|
| Magnetic Disc A | 15.2 μm | 21.0 μm | 0.72 |
| Magnetic Disc B | 20.0 μm | 30.0 μm | 0.67 |
| Magnetic Disc C | 10.4 μm | 13.5 μm | 0.77 |

By using the magnetic disc having a step h between the recording area 2 and the non-recording area 3, it becomes unnecessary to set the relation of the magnetic writing width Ww, the magnetic readout width Wr, the recording track width Tw and the track pitch Tp, to be Ww=Wr=Tw<Tp.

Accordingly, the dead zone of the tracking error signal St is decreased as compared with the conventional case by setting the dimensions of the respective portions so as to satisfy the condition indicated by Formula 1. As a result, how far the magnetic head is shifted from the center of the track is accurately detected from the tracking error signal St.

In addition, since Formula 1 is satisfied, the magnetic readout width Wr and the magnetic writing width Ww are larger than the recording track width Tw, (that is, Wr>Tw, and Ww >Tw). Since the step h is provided between the recording area 2 and the non-recording area 3, there is no magnetic effect from the non-recording region 3.

Accordingly, even though the magnetic head has its one end(a) shifted from being on the track (the center of the magnetic head is positioned on the center of the track ) toward the left side by a distance of (Wr−Tr)/2 at the time of reproduction, or even though the magnetic head has its other end(b) shifted toward the right side, the reproduction output is equivalent to the reproduction output at the time when the magnetic head is on the track as shown in FIG. 8A. Also, even though the magnetic head has its one end (a) shifted from being on the track (the center of the magnetic head is positioned on the center of the track) toward the left side by a distance of (Wr−Tr)/2 at the time of recording, or even though the magnetic head has its other end (b) shifted toward the right side by a distance of (Wr−Tw)/2 as shown in FIG. 8B, there is no failure to delete recording information previously written. Accordingly, since there is no the remaining part of the recording information at the next reproducing time, the noise component is limited to the

TABLE 1

|  | (Ts/n) < Tp | (TS/n) = Tp | (Ts/n) > Tp |
|---|---|---|---|
| Wr < Tp | −(Ts/n) − Wr + 2Tp | Tp − Wr | (Ts/n) − Wr |
| Wr = Tp | TP − (Ts/n) | 0 | (Ts/n) − Tp |
| Wr > Tp | Wr − (Ts/n) | Wr − Tp | (Ts/n) + Wr − 2Tp | minimum level and the overwrite S/N of the magnetic head is improved as compared with the conventional case.

Meanwhile, the magnetic readout width Wr and the magnetic writing width Ww of the magnetic head H do not necessarily coincide with the optically observed head width. In the present embodiment, the magnetic readout width Wr and the magnetic writing width Ww are found in the following manner.

First, the magnetic readout width Wr can be measured in the following manner. A magnetic pattern 12 having a width sufficiently smaller than the optical head width of the magnetic head to be measured is formed on a disc substrate 11, as shown in FIG. 9A. Then, a suitable signal is written over the entire width of the magnetic pattern 12 by the magnetic head.

Then, after the magnetic head to be measured is set in a position completely away from the magnetic pattern 12, the magnetic head is gradually transmitted in one direction in such a manner as to transverse the magnetic pattern 12, while the change in the output level of the reproduction signal corresponding to the change in the position of the magnetic head is sequentially plotted, as shown in FIG. 9B. Thus, a characteristic curve in the shape of trapezoid as shown in FIG. 9C can be produced. The length of a straight line connecting two points indicating ½ of the maximum output level Ymax indicates the magnetic readout width Wr of the magnetic head.

Figure 10A:
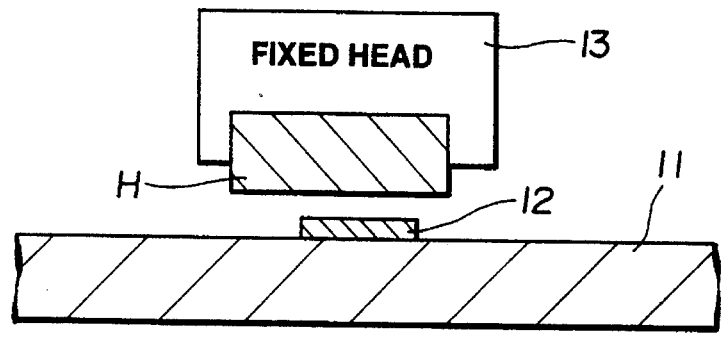
FIGS. 10A–10C show a method of measuring a magnetic writing width of the magnetic head of the magnetic disc unit of the present invention.

Next, the magnetic writing width Ww of the magnetic head can be measured in the following manner. The magnetic pattern 12 having a width sufficiently smaller than the optical head width of the magnetic head to be measured is formed on the disc substrate as shown in FIG. 10A, and then the signal written in the magnetic pattern 12 can be always read out, while a fixed head 13 having a larger width than the magnetic pattern 12 is prepared.

Figure 10B:
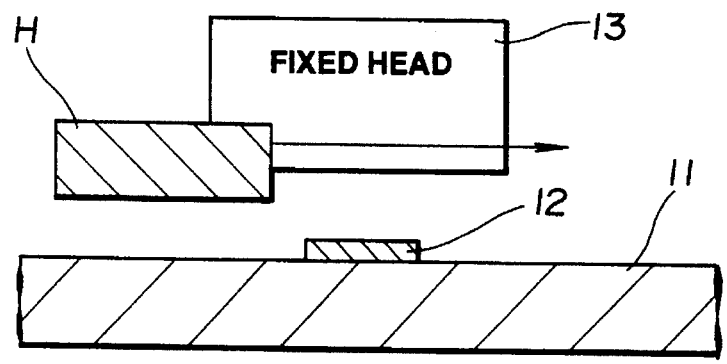

Then, as shown in FIG. 10B, after the magnetic head to be measured is set in a position completely away from the magnetic pattern 12, a suitable recording current runs through the magnetic head, and the position of the magnetic head and the reproduction signal of the fixed head 13 at this time are measured. Next, a deletion current is run through the fixed head 13, and the signal written in the magnetic pattern 12 is deleted. After that, the magnetic head to be measured is slightly moved in the direction of on-tracking the magnetic pattern 12, and while a suitable current is run through the magnetic head, the position of the magnetic head and the reproduction signal from the fixed head 13 are again measured.

Figure 10C:
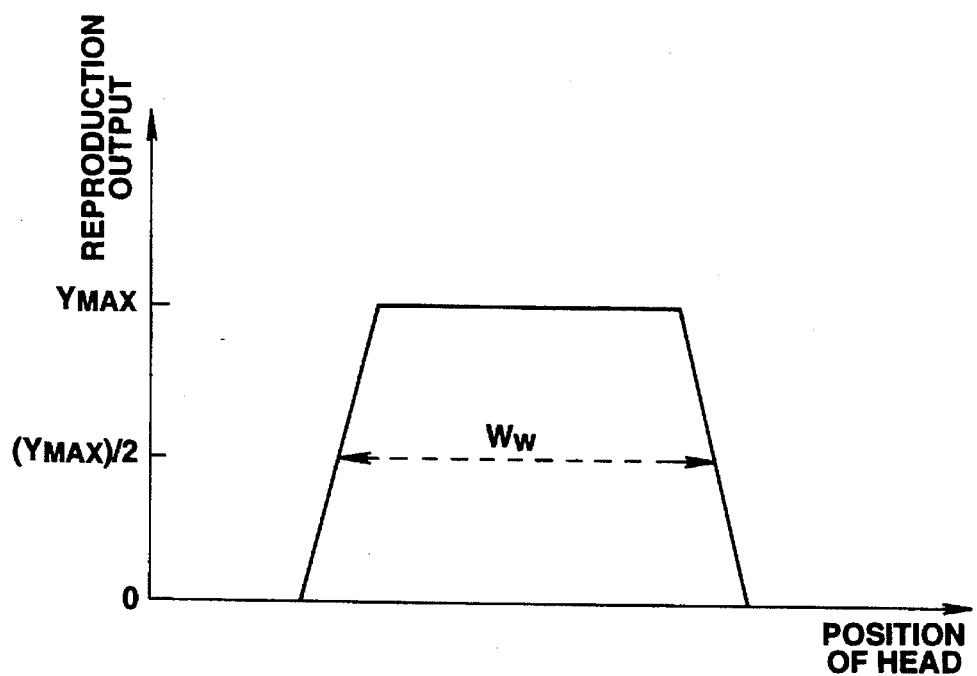

Repeating this operation, the magnetic head is gradually transmitted in one direction in such a manner as to transverse the magnetic pattern 12, and the change in the output level of the reproduction signal from the fixed head 13 corresponding to the change in the position of the magnetic head is plotted sequentially. The characteristic curve in the shape of trapezoid as shown in FIG. 10C is produced. The length of the straight line connecting two points indicating ½ of the maximum output level Ymax on the characteristic curve indicates the magnetic writing width Ww of the magnetic head.

Figure 11A:
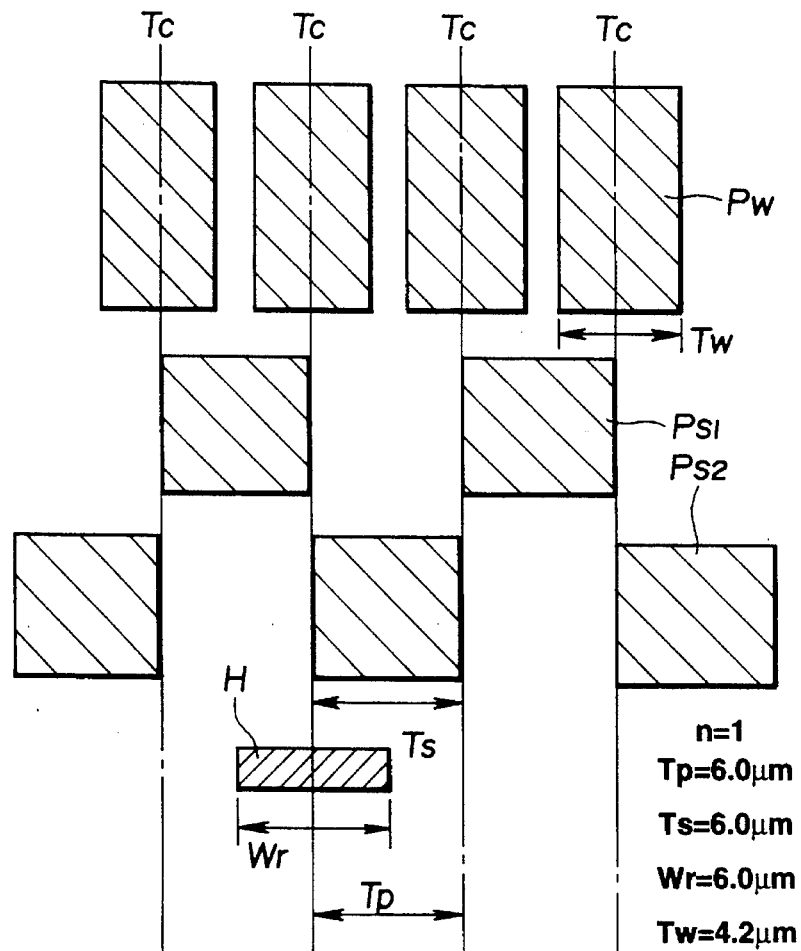
FIG. 11 shows an embodiment of the magnetic disc unit where a parameter n multiplied by an integer according to a servo pattern is set to be n=1.
Figure 11B:
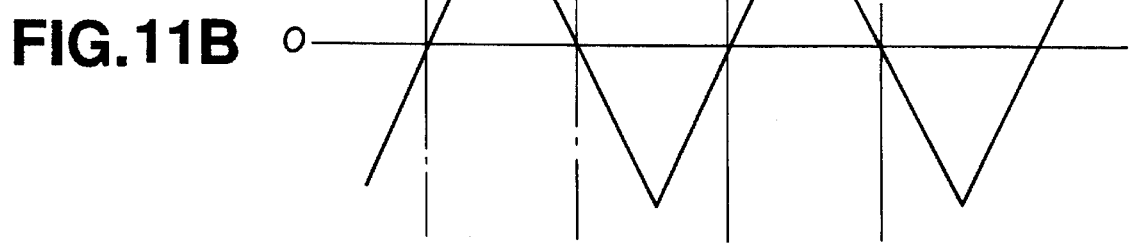
Figure 12:
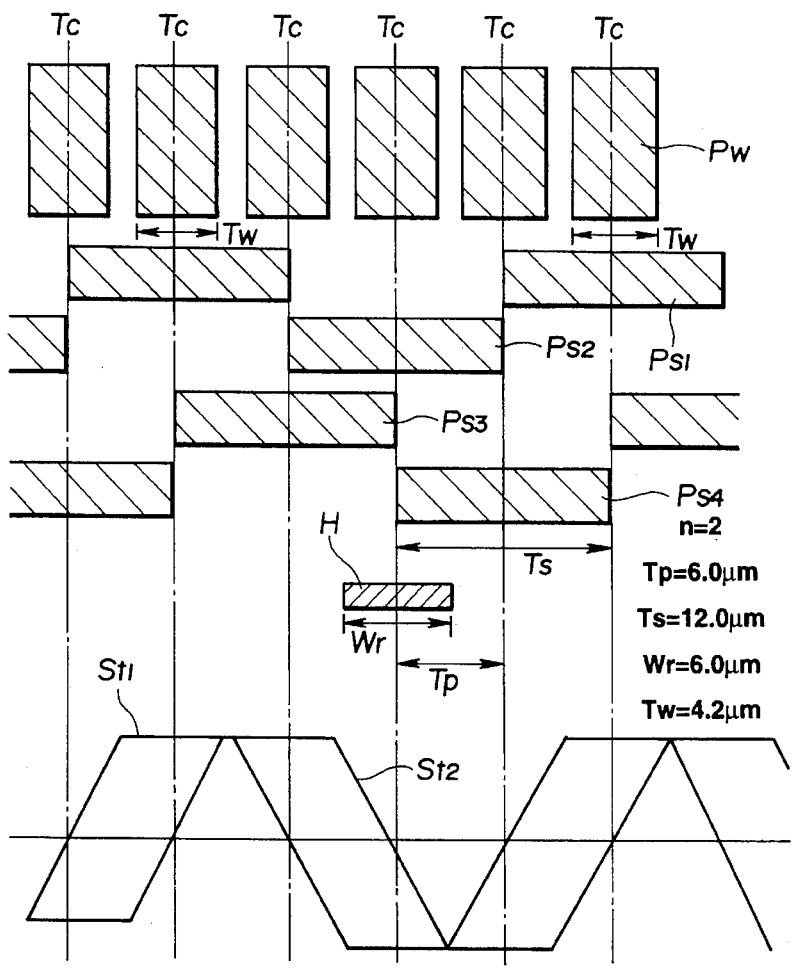
FIG. 12 shows another embodiment of the magnetic disc unit where the parameter n multiplied by an integer according to a servo pattern is set to be n=2.

An embodiment in which the magnetic readout width is set to 6.0 μm, the track pitch of the magnetic disc 1 to 6.0 μm, the servo pattern width Ts to 6.0 μm, the recording track width Tw to 4.2 μm, and n=1, is shown in FIG. 11A. Because the relation of Tp=Wr=Ts>Tw is satisfied in this embodiment, the detection signal corresponding to the position of the magnetic head is accurately output and the tracking error signal St has a signal waveform without any dead zone.

Next, another embodiment in which n is equal to 2 and the servo pattern width Ts is set to 12.0 μm, is shown in FIGURE 12A. Since n is equal to 2, four kinds of servo patterns Ps1, Ps2, Ps3, Ps4 are needed in this case. Since the width of each of the servo patterns Ps1, Ps2, Ps3, Ps4 is twice as large as that in the embodiment shown in FIG. 11A, each of the servo patterns Ps1, Ps2, Ps3, Ps4 is extended from the center of one track to the centers of tracks on both sides. Accordingly, the first servo pattern Ts1 and the second servo pattern Ts2 are arranged in a zigzag manner along the center of the track Tc passing the respective ends. The third servo pattern Ps3 and the fourth servo pattern Ps4 are arranged in a zigzag manner along the center of the track Tc passing the center of the first and second servo patterns Ps1 and Ps2.

As shown in FIG. 12B, a dead band exists in the signal waveforms of the difference (the first tracking error signal) St1 of output levels of the respective detection signals accompanying detection of the first and second servo patterns Ps1 and Ps2, and in the waveforms of the difference (the second tracking error signal) St2 of output levels of the respective detection signals accompanying detection of the third and fourth servo patterns Ps3 and Ps4. That is, when the magnetic head is in any servo pattern, the dead zone in the signal is generated.

However, the signal waveform of the second tracking error signal St2 corresponding to the dead zone of the first tracking error signal St1 is a straight line necessarily having a constant slope. Conversely, the signal waveform of the first tracking error signal St1 corresponding to the dead zone of the second tracking error signal St2 is a straight line necessarily having a constant slope. Therefore, the position of the magnetic head can be easily judged from the first and second tracking error signals St1 and St2. That is, the tracking error signal St without any dead zone is produced by suitably synthesizing the first and second tracking error signals St1 and St2.

In this manner, the dead zone in the signal is eliminated, and the magnetic head is positioned accurately and speedily in the present invention. Accordingly, it is possible to carry out the movement of the magnetic head in the direction of diameter at the time of reproducing data of a demanded address (sector) or recording data in the address (sector), that is, step jump operation, track jump operation and seek operation. The time for access to data is reduced.

In addition, there is no dead band in the tracking error signal St indicating the position of the magnetic head, and its linear slope in the signal waveform is constant. Therefore, the controllability of positioning control for the magnetic head H by the servo circuit is good.

Also, since the magnetic disc 1 having the step h between the recording area 2 non-recording area 3 is used, the magnetic effect from the non-recording region 3 is eliminated. Thus, even when the position of the magnetic head is off the track from the recording track pattern Pw because of an external vibration, there is no trouble caused in recording and reproduction of data. Accordingly, even though the magnetic disc unit is vibrated, it is possible to carry out recording and reproduction in good conditions with a low error rate.

Thus it is apparent that in accordance with the present invention, an apparatus that fully satisfies the objectives, aims and advantages is set forth above. While the invention has been described in conjunction with specific embodiments, it is evident that many alternatives, modifications, permutations and variations will become apparent to those skilled in the art in light of the foregoing description.

Accordingly, it is intended that the present invention embrace all such alternatives, modifications and variations as fall within the scope of the appended claims.

I claim:

1. A magnetic disc unit, comprising:

a magnetic recording medium having a servo region and a data region alternately allocated, the servo region having a servo pattern with a servo pattern width Ts, the data region having a recording track pattern with a track pitch Tp and a recording track width Tw, having a step between a recording area and a non-recording area thereon;

a magnetic head with a magnetic writing width of Ww and a magnetic readout witdth of Wr;

wherein a relation between said recording track width Tw and said magnetic readout width Wr is Wr>Tw, while a relation between said recording track width Tw and said magnetic writing wideth Ww is Ww>Tw;

wherein a relation between said servo pattern width Ts and said track Tp is set to be Tp (n−0.1) ≦Ts≦Tp(n+ 0.1), where n is a positive, non-zero integer; and wherein a relation between said magnetic readout width Wr and said track pitch Tp is set to be 0.9 Tp≦Wr≦1.1 Tp, wherein a dead zone in a tracking error signal produced from said magnetic recording medium is substantially eliminated.

2. The magnetic disc unit according to claim 1, wherein said step is created by first depositing a layer of magnetic material on a surface of said recording medium and then etching away the magnetic material in selected areas.

3. The magnetic disc unit according to claim 1, wherein said step is created by forming a step on a surface of said recording medium and then depositing a layer of magnetic material on said surface.

4. The magnetic disc unit according to claim 1, wherein said recording medium includes a flexible disc.

5. The magnetic disc unit according to claim 1, wherein said recording medium includes a hard disc.

6. A magnetic disc unit comprising:

a magnetic recording medium having a servo region and a data region alternately allocated, the servo region having a servo pattern with a servo pattern width Ts, the data region having a recording track pattern with a track pitch Tp and a recording track width Tw, having a step between a recording area and a non-recording area thereon;

a magnetic head with a magnetic writing width of Ww and a magnetic readout width of Wr;
wherein said magnetic readout width Wr is approximately equal to said track pitch Tp;

wherein said servo pattern width Ts is approximately equal to said track pitch Tp or an integer multiple thereof;

wherein a relation between said servo pattern width Ts and said track pitch Tp is set to be Tp(n−0.1)≦Ts≦Tp(n+0.1), and a relation between said magnetic readout width Wr and said track pitch Tp is set to be 0.9 TP≦Wr≦1.1 Tp, where n is a positive, non-zero integer; and wherein a relation between said recording track width Tw and said magnetic readout width Wr is Wr>Tw, while a relation between said recording track width Tw and said magnetic writing width Ww is Ww>Tw, wherein a dead zone in a tracking error signal is substantially eliminated.

7. The magnetic disc unit according to claim 6, wherein said step is created by first depositing a layer of magnetic material on a surface of said recording medium and then etching away the magnetic material in selected areas.

8. The magnetic disc unit according to claim 6, wherein said step is created by forming a step on a surface of said recording medium and then depositing a layer of magnetic material on said surface.

9. The magnetic disc unit according to claim 6, wherein said recording medium includes a flexible disc.

10. The magnetic disc unit according to claim 6, wherein said recording medium includes a hard disc.

11. A magnetic disc of a magnetic disc unit having a magnetic head with a magnetic writing width of Ww and a magnetic readout width of Wr, said magnetic disc comprising:

a magnetic recording medium having a servo region and a data region alternately allocated, the servo region having a servo pattern with a servo pattern width Ts, the data region having a recording track pattern with a track pitch Tp and a recording track width Tw, and a having a step between a recording area and a non-recording area thereon;

wherein a relation between said recording track width Tw and said magnetic readout width Wr is Wr>Tw, while a relation between said recording track width Tw and said magnetic writing width ww is Ww>Tw;

wherein a relation between said track pitch Tp and said magnetic readout width Wr is set to be 0.9 Tp≦Wr≦1.1 Tp; and wherein a relation between said servo pattern width Ts and said track pitch Tp is set to be Tp(n−0.1)≦Ts≦Tp(n+0.1), where n is a positive, non-zero integer, wherein a dead zone in a tracking error signal produced from said magnetic recording medium is substantially eliminated.

12. The magnetic disc unit according to claim 11, wherein said recording medium includes a flexible disc.

13. The magnetic disc unit according to claim 11, wherein said recording medium includes a hard disc.

14. The magnetic disc according to claim 11, wherein said step is created by first depositing a layer of magnetic material on a surface of said recording medium and then etching away the magnetic material in selected areas.

15. The magnetic disc unit according to claim 11, wherein said step is created by forming a step on a surface of said recording medium and then depositing a layer of magnetic material on said surface.

16. A magnetic disc of a magnetic disc unit having a magnetic head with a magnetic writing width of Ww and a magnetic readout width of Wr, said magnetic disc comprising:

a magnetic recording medium having a servo region and a data region alternately allocated, the servo region having a servo pattern with a servo pattern width Ts, the data region having a recording track pattern with a track pitch Tp and a recording track width Tw, having a step between a recording area and a non-recording area thereon;

wherein said track pitch Tp is approximately equal to said magnetic readout width Wr;

wherein said servo pattern width Ts is approximately equal to said track pitch Tp or an integer multiple thereof;

wherein a relation between said servo pattern width Ts and said track pitch Tp is set to be Tp(n−0.1)≦Ts≦Tp(n+0.1), where n is a positive, non-zero integer, and a relation between said magnetic readout width Wr and said track pitch Tp is set to be 0.9 Tp≦Wr≦1.1 Tp; and wherein a relation between said recording track width Tw and said magnetic readout width Wr is Wr>Tw, while a relation between said recording track width Tw and said magnetic writing width Ww is Ww>Tw, wherein a dead zone in a tracking error signal produced from said magnetic recording medium is substantially eliminated.

17. The magnetic disc according to claim 16, wherein said step is created by first depositing a layer of magnetic material on a surface of said recording medium and then etching away the magnetic material in selected areas.

18. The magnetic disc unit according to claim 16, wherein said step is created by forming a step on a surface of said recording medium and then depositing a layer of magnetic material on said surface.

19. The magnetic disc unit according to claim 16, wherein said recording medium includes a flexible disc.

20. The magnetic disc unit according to claim 16, wherein said recording medium includes a hard disc.

* * * * *